United States Patent [19]

Jackson et al.

[11] Patent Number: 4,615,696
[45] Date of Patent: Oct. 7, 1986

[54] SANITARY NAPKIN WITH FOLDED COVER

[75] Inventors: David M. Jackson, Fulton County, Ga.; Donald A. Sheldon, Outagamie County, Wis.

[73] Assignee: Kimberly-Clark Corporation, Neenah, Wis.

[21] Appl. No.: 605,335

[22] Filed: Apr. 30, 1984

[51] Int. Cl.$^4$ .............................................. A61F 13/16
[52] U.S. Cl. .................................... 604/389; 604/390; 604/370
[58] Field of Search ............... 604/370, 366, 385, 389, 604/390

[56] References Cited
U.S. PATENT DOCUMENTS 3,595,237  7/1971  Sargent ................................ 604/366
3,672,371  6/1972  Roeder ................................. 604/373
3,913,579  10/1975  Srinivasan et al. ................. 604/366
4,100,324  7/1978  Anderson et al. .................. 604/374

Primary Examiner—C. Fred Rosenbaum
Assistant Examiner—Sherri E. Vinyard
Attorney, Agent, or Firm—Paul A. Leipold; Donald L. Traut; J. J. Duggan

[57] ABSTRACT

A sanitary napkin is provided which contains an absorbent core layer which is overlayed on its top and bottom surface with a secondary layer of reduced absorbency. The secondary layer has abutting faces adjacent each other on the bottom sides of the napkin. Adhesive is applied to a strip of nonwoven material which is positioned above the parallel faces of the bottom layer to maintain the napkin configuration.

3 Claims, 4 Drawing Figures

U.S. Patent  Oct. 7, 1986  4,615,696

SANITARY NAPKIN WITH FOLDED COVER

FIELD OF THE INVENTION

This invention relates to a sanitary napkin and particularly to a sanitary napkin having multiple layers of different components.

BACKGROUND OF THE INVENTION

Recently, sanitary napkins have been developed which contain components other than wood pulp fluff, a fluid pervious cover, and a fluid impermeable baffle. The inclusion of materials with heightened absorbent capabilities but reduced bulk such as superabsorbent materials and surfactant treated meltblown microfiber webs have allowed the production of thin sanitary napkins with adequate capacity. Furthermore, it has been recognized that sanitary napkins which contain wood pulp fluff or similar cellulosic absorbent material can benefit from the addition or substitution in part of a layer of material containing thermoplastic fibers. Conventional cellulosic absorbents, when wet, are extremely uncomfortable because cellulosic capillaries tend to collapse with the addition of fluid. To overcome this tendency, multilayer napkins have been constructed in which a layer overlying the wood pulp fluff layer incorporates thermoplastic fibers. These fibers are more hydrophobic than cellulosic fibers and capillaries formed by these fibers do not collapse when wet. Because of the inclusion of the fibers, however, there may be a reduced capacity when compared to the conventional cellulosic fibers and this is certainly the case when a layer containing both thermoplastic and wood pulp fibers are compared to absorbent material such as superabsorbents.

U.S. Pat. No. 4,100,324 discloses a process for making a cover material for a sanitary napkin which is a turbulently airlaid mixture of wood pulp fluff fibers and meltblown microfibers. The merging of separate streams of these fibers producing a turbulent air flow results in a web with ample integrity. The properties of this web may be manipulated by varying such things as its basis weight, the amount, diameter, and type of meltblown microfibers employed as well as the relationship of such a web to other components in a sanitary napkin. It is apparent that by manipulating these properties the absorbency, the tactual properties and the z direction transfer of the web can be manipulated over a substantial range.

NEW FREEDOM ® Maxithins sanitary napkins have recently been marketed which employ a coformed web as an intermediate layer between nonwoven cover material and a surfactant treated meltblown microfiber layer.

The additional nonwoven layer is needed because of the difficulty in obtaining adhesive bonding through an overlapped layer of the coform material.

As disclosed in U.S. Pat. No. 3,672,371, issued to Robert J. Roeder, a pressure sensitive garment attachment adhesive can be employed which attaches a sanitary napkin to a garment and penetrates and seals the overlapped portion of the wrap of a sanitary napkin. Due to the comparatively thick dense nature of the coform layer compared to the nonwoven wrap, adhesive will not readily penetrate and also serve the garment attachment function.

SUMMARY OF THE INVENTION

According to this invention a sanitary napkin containing an absorbent core layer and a second thermoplastic fiber containing layer surrounding the absorbent core can be made without the addition of a separate nonwoven wrap by designing the width of the folded thermoplastic containing intermediary layer such that it provides two adjacent parallel faces which do not overlap each other. A relatively narrow strip of nonwoven material is provided so that it overlays the butting faces of the intermediate layer. The thin strip of nonwoven material is attached to the butting surfaces of the intermediate layer with an adhesive which also serves to maintain the butted portion in place. Preferably this adhesive is pressure sensitive and will serve as garment attachment adhesive eliminating the need for subsequent adhesive means.

The invention may more readily understood by reference to the drawings in which.

Figure 1:
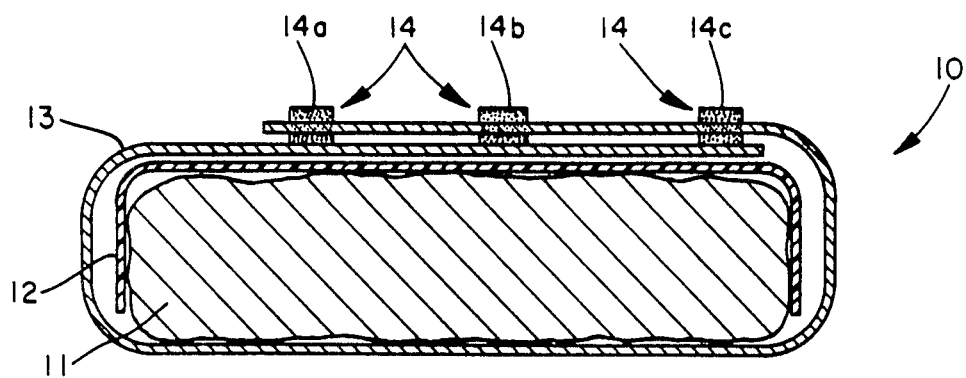
FIG. 1 is an end diagrammatic view partially in cross section of a sanitary napkin with an absorbent core and a nonwoven cover.
Figure 2:
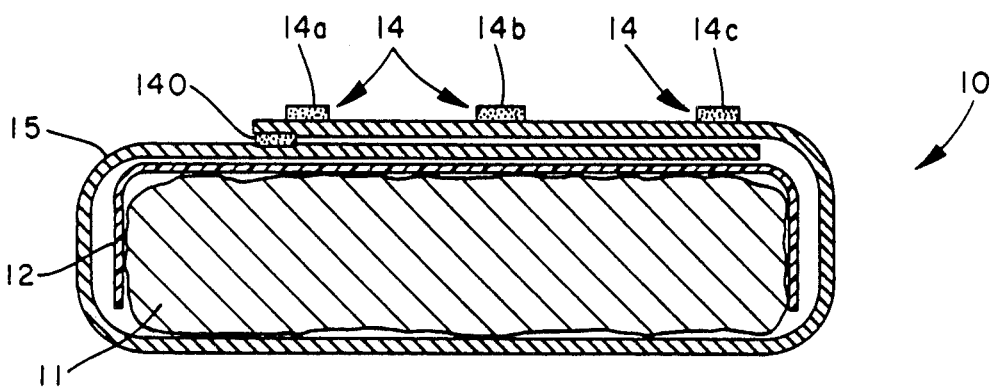
FIG. 2 is an end diagrammatic view partially in cross section of a sanitary napkin with an absorbent core and a nonwoven cover showing an adhesive configuration required by application of an overlapped intermediate layer as a cover.
Figure 3A:
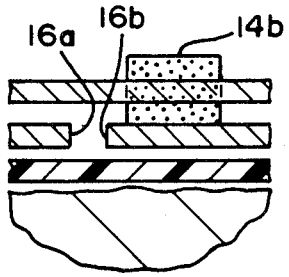
FIG. 3A is an enlarged cross sectional view of the adhesive taken along line 3A of FIG. 3.
Figure 3:
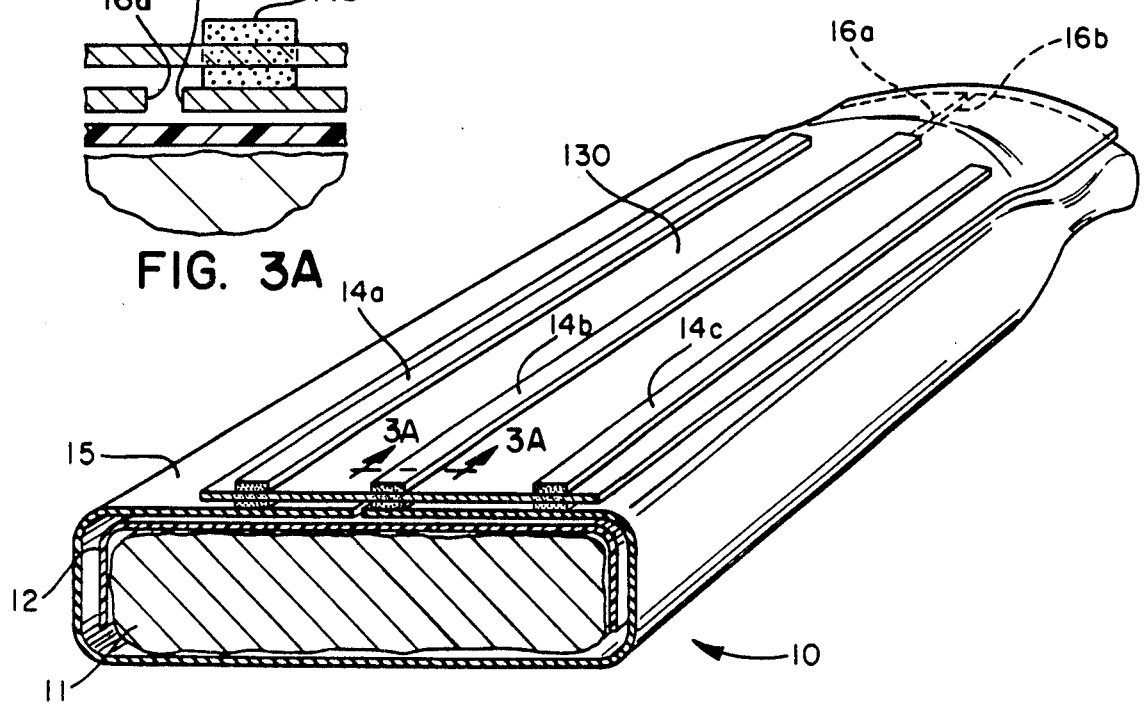
FIG.3 is an end diagrammatic view partially in cross section of a sanitary napkin with an absorbent core and a nonwoven cover a view of the configuration of this invention.

As can be seen from FIG. 1, a sanitary napkin containing an absorbent core 11 has a fluid impermeable baffle 12 positioned on the bottom and sides of the absorbent core layer 11. A nonwoven cover material such as spunbonded polypropylene overwraps both the absorbent core layer 11 and the baffle 12 and is adhesively sealed to itself by three parallel garment adhesive lines 14 which act to attach the napkin to the undergarment of the wearer as well as to seal the overlapped portion of the wrap. When a relatively higher weight wrap of increased density such as coformed material is used it is impossible to obtain the penetration of garment adhesive 14 through the coform layer 15 and in this instance a separate adhesive application is necessary as shown by adhesive line 140.

According to this invention, rather than overlap the intermediate layer, the intermediate layer is of a width sufficient to provide butting or nearly touching parallel faces extending along the bottom or garment facing side of the napkin profile. These faces 16a and b are overlaid by a thin nonwoven cover overlap material 130 and adhesively bonded to this intermediate layer 15. Pressure sensitive garment adhesive strips are added to penetrate the nonwoven cover, 130 attach the cover to the overlapped intermediate layer, 15 and also provide for garment attachment when the napkin is used. The central adhesive line 14b is shown as positioned inward of face 16b but may in fact rest upon butting faces 16a and 16b although due to the presence of the outboard adhesive lines 14a and c the precise positioning of this line is not critical.

Because of the ability to design an intermediate layer for specific product applications, no further wrap may be needed. A currently preferred configuration utilizes a six inch wide intermediate wrapping layer with a one and one-half inch wide nonwoven cover overlap centrally positioned on the bottom or garment facing side of the napkin. In a further varient of the invention, the nonwoven strip may be extended to each napkin end and be ultrasonically bonded thereto.

It is also contemplated to fuse the cover material to the intermediate layer thus providing a surface in which a substantially reduced amount of adhesive may be used for garment attachment. This fusing may of course be done by ultrasonic means as is well known in the art.

We claim:

1. A sanitary napkin comprising in combination:
   (a) an elongate absorbent core layer with a substantially planar body facing surface and an opposite substantially planar garment facing surface;
   (b) a wrapping layer overlying substantially both surfaces of said absorbent layer with said layer having two parallel longitudinally extending edge faces adjacent each other in butting or nearly touching, but not overlapping, arrangement of said parallel faces overlying said garment facing surface and essentially traversely, centrally disposed with respect to said garment facing surface, said wrapping layer having reduced absorbent capacity per unit weight relative to said absorbent layer;
   (c) an elongate strip of thin adhesive permeable nonwoven material overlying said adjacent parallel edge faces of said wrapping layer; and
   (d) pressure-sensitive adhesive strips which anchor said nonwoven strip to each of said parallel edge faces and provide for garment attachment when said napkin is used.

2. The napkin according to claim 1 wherein the wrapping layer contains thermoplastic fibers.

3. The napkin according to claim 2 wherein the wrapping layer contains coform, a mixture of turbulently formed pulp and meltblown microfibers.

* * * * *